US00PP10783P

United States Patent [19]

Akerboom

[11] Patent Number: Plant 10,783

[45] Date of Patent: Feb. 9, 1999

[54] ASTER PLANT NAMED 'PETER'S WHITE'

[75] Inventor: Petrus J. Akerboom, Ter Aar, Netherlands

[73] Assignee: De Nachtvlinder B.V., Ter Arr, Netherlands

[21] Appl. No.: 839,493

[22] Filed: Apr. 14, 1997

[51] Int. Cl.[6] ..... A01H 5/00

[52] U.S. Cl. ..... Plt./68.1

[58] Field of Search ..... Plt./68.1

[56] References Cited

PUBLICATIONS

GTITM UPOVROM Listing for 'Peter's White' as per PBR 02616 (IL), Aug. 6, 1996.

GTITM UPOVROM Listing for 'Peter's White' as per PBR 9338 (JP), Dec. 24, 1996.

*Primary Examiner*—Howard J. Locker
*Assistant Examiner*—Kent L. Bell
*Attorney, Agent, or Firm*—Foley & Lardner

[57] ABSTRACT

A new and distinct cultivar of aster plant named 'Peter's White', characterized by its white ray floret color; short flowering height; elliptic-linear shaped leaved which are medium to long in length, dark green in color and sometimes with a slight anthocyanin coloration; first flower heads spread along the axis; medium to large flower heads with many ray florets; medium to long ray florets that are narrowly elliptic in shape; long, cylindrical shaped involucre; and late flowering.

2 Drawing Sheets

The present invention comprises a new and distinct cultivar of Aster plant hereinafter referred to by the cultivar name 'Peter's White'.

BACKGROUND OF THE INVENTION

The new cultivar was originated from a cross made in a controlled breeding program in Ter Aar, Holland. The female or seed parent was a selection from proprietary breeding stock designated the "Butterfly family" while the male or pollen parent was a selection from proprietary breeding stock designated the "P" family. 'Peter's White' was discovered and selected by the inventor as a flowering plant within the progeny of the stated cross in a controlled environment in Ter Aar, Holland. First asexual reproduction of the new cultivar by cuttings was in December 1994. Subsequent asexual reproduction by cuttings of the new cultivar as performed by applicant at Ter Aar, Holland, has demonstrated that the combination of characteristics as herein disclosed are firmly fixed and retained through successive generations.

'Peter's White' has not been observed under all possible environmental conditions. The phenotype may vary with variations in environment such as temperature, light intensity and day length, without only change in the genotype of the plant. The following observations, measurements and values describe the new cultivar as grown in Ter Aar, Holland under conditions which closely approximate those generally used in commercial practice.

The new cultivar is most similar to 'Milka' , U.S. Plant Patent application Ser. No. 8/664,519) 'Karmijn' U.S. Plant Patent application Ser. No. 8/664,520, and 'Parade' U.S. Plant Patent application Ser. No. 8/664,669, each of the cultivars has a similar number of ray florets and type of flower head. The following Table provides several phenotypic characteristics that can be used to distinguish the aster varities 'Parade', 'Milka', 'Karmijn', and 'Peter's White'.

| | Ray Florets | | | Capitulum | |
|---|---|---|---|---|---|
| | Color (RHS) | Length (mm) | Diameter (mm) | Diameter (mm) | Shape |
| 'Parade' | Purple (87A) | 11–13 | 1.8 | 28–30 | Funnel-shaped, Long |
| 'Milka' | Violet (85A) | 14–16 | 2.0 | 24–27 | Cylindrical, Very Long |
| 'Karmijn' | Purple-Violet (81B) | 12–15 | 2.0 | 26–29 | Campanulate, Medium Length |
| 'Peter's White' | White (155B) | 11–13 | 2.0 | 26–30 | Cylindrical, Very Long |

BRIEF SUMMARY OF THE INVENTION

The following traits have been repeatedly observed and are determined to be basic characteristics of 'Peter's White' which in combination distinguish this aster as a new and distinct cultivar:

1) As flowering commences 'Peter's White' is very short to short.

2) Leaves are elliptic-linear shaped, medium to long in length, dark green in color without anthocyanin coloration.

3) The first flower heads produced are spread along the axis.

4) The flower head is medium to large in size with many ray florets.

5) The ray florets are medium to long in size and narrowly elliptic in shape.

6) The involucre is cylindrical in shape and very long.

7) Flowering commences very late compared to other asters.

BRIEF DESCRIPTION OF THE DRAWINGS

The accompanying photographic drawing shows a typical specimen plant of the new cultivar. The colors appearing in the photograph are as true as possible with color illustrations of this type.

Sheet 1 is a side view of a pot culture specimen of 'Peter's White'.

Sheet 2 is a side view of a flower production specimen of 'Peter's White'.

DETAILED BOTANICAL DESCRIPTION

In the following description, color references are made to The Royal Horticultural Society Color Chart (R.H.S.), except where general colors of ordinary significance are referred to. Color values were taken indoors under north light conditions at approximately 12 noon in Nieuwveen, Holland.

Classification:
*Botanical.*—*Aster Novi-belgii* L.
*Commerical.*—'Peter's White'.
Parentage:
*Male parent.*—Proprietary selection from Butterfly family.
*Female parent.*—Proprietary selection from P family.
Propagation: The new cultivar maintains its distinguishing characteristics through successive propagations by cuttings.

Inflorescence

Capitulum:
*Form.*—Convex.
*Type.*—Double.
*Diameter across face.*—26–30 mm (average 28–29 mm).
B. Corolla of ray florets:
*Color* (*general tonality from a distance of three meters*) .—White.
*Color* (*upper surface*).—White R.H.S. 155B.
*Color* (*under surface*).—White R.H.S. 155B.
*Shape.*—Narrow, elliptic, with acute to round tip.
*Size of floret.*—11–13 mm length×2 mm width
*Number of florets.*—125–759.
C. Corolla of disc florets: 'Peter's White' doesn't produce disc florets, instead of disc florets there are ray florets.
D. Reproductive organs:
*Androecium.*—Not always present the variety does not appear to produce pollen.
*Gynoecium.*—Present.
E. Buds:
*Size.*—Just before opening approximately 8 mm diameter.
*Color.*—Dark green R.H.S. 137A.

II. Plant

A. General appearance: The plants are very short to short in height as flowering commences. The leaves produced by 'Peter's White' are elliptic-linear in shape, medium to long in length and are dark green in color. The first flower heads produced are spread along the axis. The flower head is medium to large in size with many ray florets. The ray florets are medium to long in size and narrowly elliptic in shape. The involucre is cylindrical in shape and very long. Flowering commences very late compared to other asters; the flowering period is from June through February, in which the cultivar flowers only twice. The stem is pubescent. The plant has a high density of branching.
*Height.*—Short to very short; 1.2 meters for flower production and 10–15 cm for pot culture.
*Stem.*—Length (mm) of internode (first internode is first sideflower under top flower):

| INTERNODE | | | |
|---|---|---|---|
| 5th | 10th | 15th | 20th |
| 10–18 | 22–26 | 28–32 | 23–31 |

Thickness (mm) of internode (first internode is first sideflower under top flower):

| INTERNODE | | | |
|---|---|---|---|
| 5th | 10th | 15th | 20th |
| 1.4–1.8 | 1.8–2.5 | 2.6–3.2 | 3.5–4.8 |

B. Foliage:
*Color.*—Dark green R.H.S. 137A.
*Length* (*maximum in mm; first internode is first sideflower under top flower*).—

| INTERNODE | | | |
|---|---|---|---|
| 5th | 10th | 15th | 20th |
| 52–70 | 72–90 | 87–110 | 106–128 |

*Width* (*maximum in mm; first internode is first sideflower under top flower*).—

| INTERNODE | | | |
|---|---|---|---|
| 5th | 10th | 15th | 20th |
| 7.0–9.0 | 8.6–12.0 | 11.2–14.2 | 12.1–16.0 |

*Margin.*—Almost no indentations.
*Shape.*—Elliptic-linear, medium to long in length.
*Arrangement.*—Strong leaves.
*For flower production.*—Long day treatment until plant is approximately 50 cm tall. After that approximately 5.5 weeks short day treatment.
*For pot culture.*—Directly after rooting and/or topping 1 or more times 5–6 weeks short day treatment.
C. Side branch:
*Length* (*maximum in mm; first internode is first sideflower under top flower*).—

| INTERNODE | | | |
|---|---|---|---|
| 5th | 10th | 15th | 20th |
| 46–65 | 85–142 | 150–242 | 195–414 |

D. Disease resistance: No unusual disease resistance has been exhibited by this cultivar when compared to other known commerical aster varieties.

E. Fertility: Irregular fertility because the variety does not appear to produce pollen.

*Fragrance.*—None.

I claim:

1. A new and distinct cultivar of aster plant named 'Peter's White', as illustrated and described.

* * * * *

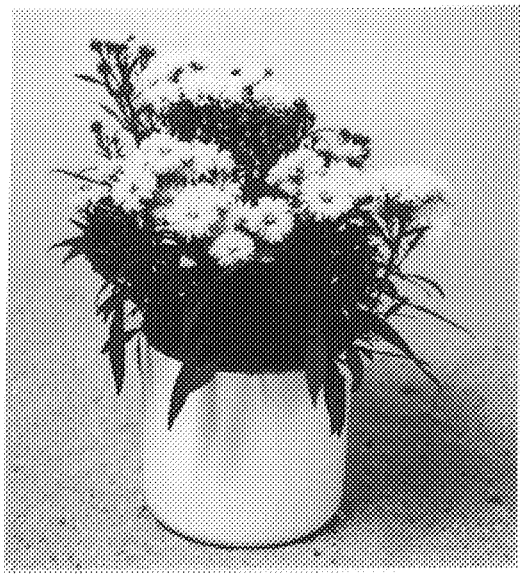

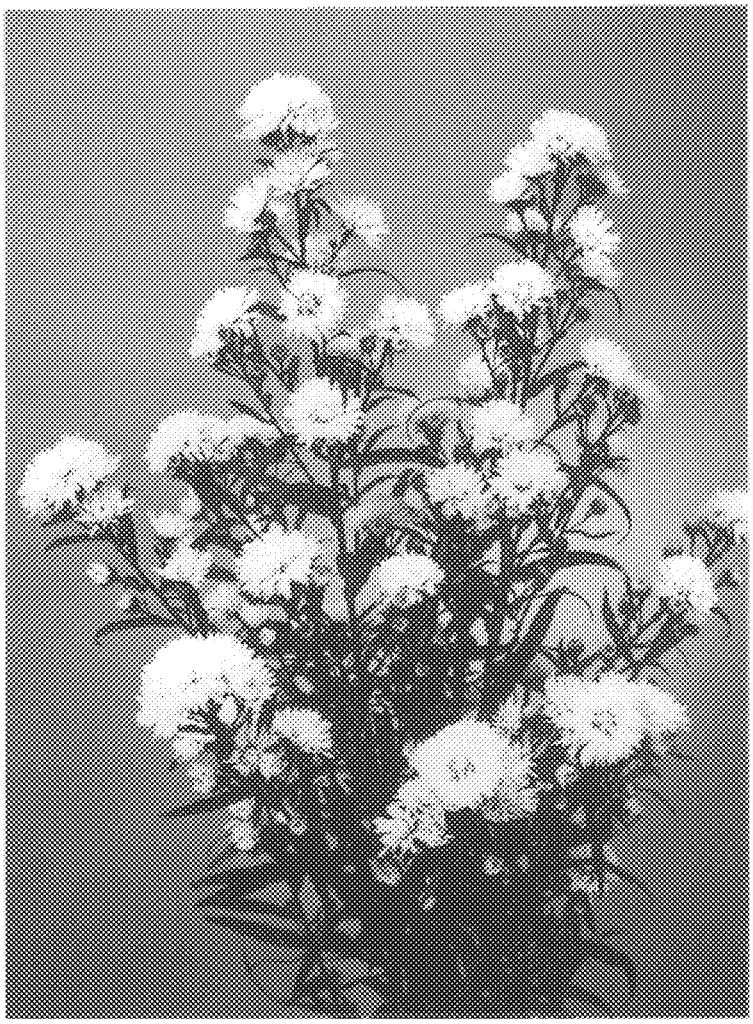

UNITED STATES PATENT AND TRADEMARK OFFICE

CERTIFICATE OF CORRECTION

PATENT NO. : Plant 10-783

DATED : February 9, 1999

INVENTOR(S) : Petrus J. AKERBOOM

It is certified that error appears in the above-identified patent and that said Letters Patent is hereby corrected as shown below:

On the title page, item [73] Assignee, change "Ter Arr" and replace with --Ter Aar--.

Signed and Sealed this

Twenty-second Day of August, 2000

*Attest:*

Q. TODD DICKINSON

*Attesting Officer*

*Director of Patents and Trademarks*